(12) United States Patent
Tottenham et al.

(10) Patent No.: US 6,264,889 B1
(45) Date of Patent: Jul. 24, 2001

(54) APPARATUS AND METHOD FOR FOOD PROCESSING EQUIPMENT MICROBIAL INTERVENTION AND PASTEURIZATION

(76) Inventors: Dennis E. Tottenham, 10430 Gulfdale, San Antonio, TX (US) 78216; David E. Purser, 906 Riverstone Dr., San Antonio, TX (US) 78258

(*) Notice: Subject to any disclaimer, the term of this patent is extended or adjusted under 35 U.S.C. 154(b) by 0 days.

(21) Appl. No.: 09/662,782

(22) Filed: Sep. 15, 2000

Related U.S. Application Data

(63) Continuation-in-part of application No. 09/464,031, filed on Dec. 15, 1999, now Pat. No. 6,153,240.

(51) Int. Cl.$^7$ .................................................. A61L 2/00
(52) U.S. Cl. ........................... 422/26; 134/18; 134/30; 134/56 R; 134/72
(58) Field of Search .................... 422/26, 116, 300; 134/18, 30, 56 R, 68, 72

(56) References Cited

U.S. PATENT DOCUMENTS 5,132,084 * 7/1992 Harrell et al. ..................... 422/26
5,997,813 * 12/1999 Yaskoff et al. .................... 422/26

* cited by examiner

*Primary Examiner*—George C. Yeung
(74) *Attorney, Agent, or Firm*—Jenkens & Gilchrist A Professional Corporation

(57) ABSTRACT

An apparatus and method for microbial intervention and pasteurization of food processing equipment. The apparatus comprises a chamber, a steam generator, a controller, a timer, a power source, and a temperature sensor. The temperature sensor, along with the timer, is used to control the exposure of food processing equipment to steam. After a controlled period of steam application, a chilled water source is used to bathe the food processing equipment. The method includes the steps of placing food processing equipment in the chamber, adding steam to the chamber, continuing to add steam until the surface of the food processing equipment is greater than a first preselected temperature, maintaining the surface temperature by the continued application of steam for a period of about 60 seconds or until it is greater than a second preselected temperature, and then bathing the outer surface of the food processing equipment with chilled water for about 60 seconds. The use of this method results in a 5-log reduction in the population of microorganisms and bacteria on the surface of the food and/or equipment.

34 Claims, 8 Drawing Sheets

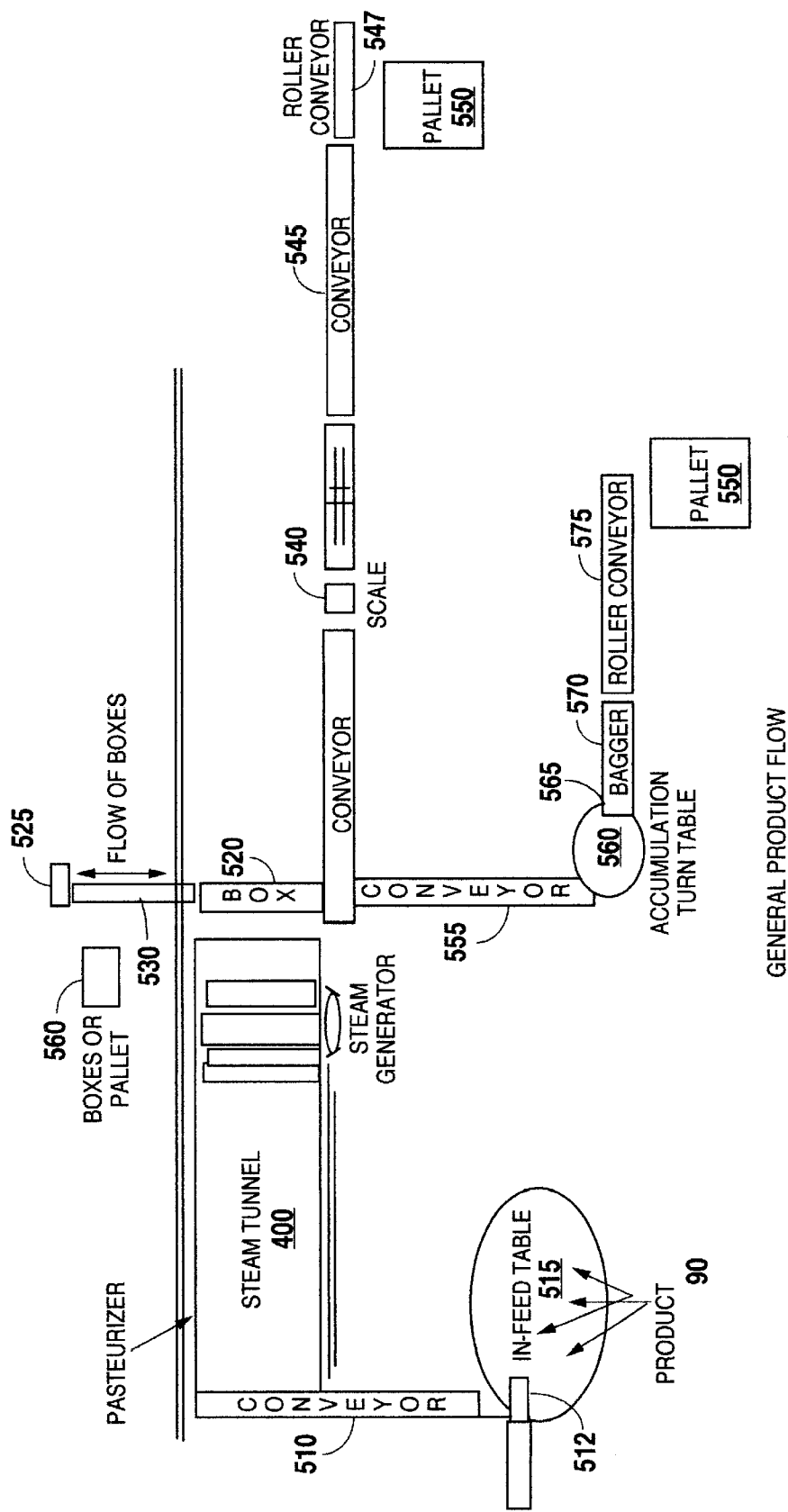

APPARATUS AND METHOD FOR FOOD PROCESSING EQUIPMENT MICROBIAL INTERVENTION AND PASTEURIZATION

RELATED APPLICATIONS

This application is a continuation-in-part of application Ser. No. 09/464,031 filed on Dec. 15, 1999, now U.S. Pat. No. 6,153,240.

BACKGROUND OF THE INVENTION

1. Technical Field

The present invention generally relates to systems and methods for cleaning food and food processing equipment, and more particularly, to a surface microbial intervention system and method that provide a 5-log (i.e., 100,000 times) reduction in the amount of microbial pathogens on the surface of food products and other items, such as food processing equipment.

2. History of Related Art

Fruits, vegetables, and other foods are allowed to remain in contact with soil, insects, and animals during the time of their growth and harvest. Thus, fresh produce, for example, maintains populations of $10^4$ and $10^5$ microorganisms/gram when they arrive at the packing house. Such microorganisms include coliform bacteria, including Enterobacter, Klegsiella spp., and *Escherichia coli*. The bacteria population tends to remain relatively stable, with no significant influence exerted by temperature, total precipitation, or length of the day during harvest. Such bacteria may become natural contaminants of frozen concentrated fruit juices.

Since improperly handled food products and processing equipment can serve as a vehicle for the transmission of microorganisms to humans, the elimination of such surface bacteria and pathogenic microbes (which include spoilage organisms) has a tremendous value to the food and health industries. For example, there is currently a requirement by the Food and Drug Administration and the United States Department of Agriculture that all juice products include the following warning statement on package labels after Nov. 5, 1999.

WARNING: This product has not been pasteurized and, therefore, may contain harmful bacteria that can cause serious illness in children, the elderly, and persons with weakened immune systems.

Thus, there are not only safety hazards afforded by the presence of these surface contaminants, but also marketing and legal implications.

Several approaches to reducing the number of bacteria on the surface of produce, food products, and food processing equipment have been attempted. Common chemical sanitizers, such as chlorine treatments, may be reasonably effective for equipment sanitation, but these chemicals apparently have little effect on microorganisms. Another approach includes steaming herbs, spices, and root/tuber vegetables under pressure, or in a vacuum. Chemical gases may be used to create an antiseptic environment. Each of these processes tends to be expensive and unreliable, fraught with an abundance of complicated equipment which tends to break down, and produce unpredictable results.

Even when simple steam is applied to provide microbial intervention at the surface of food products and processing equipment, it is often the case that expensive and complicated steam generation apparatus is used. Further, the methods of steam production often involve holding times that are overly long; such immersion in steam or hot water tends to adversely affect the organoleptic properties of the food products so treated.

Therefore, what is needed, is an apparatus and method for microbial intervention and pasteurization of food product and food processing equipment surfaces which is inexpensive and mechanically simple. Further, the apparatus and method should produce repeatable, reliable results. More specifically, the holding time for the food products to be surface pasteurized should be consistently maintained at the minimum level necessary to accomplish a 5-log reduction in the amount of surface bacteria and/or microorganisms present on external surfaces of the food and processing equipment. A minimum number of steps to implement the process of such a method should be required, and preferably, no special chemicals should be introduced into the microbial intervention process.

SUMMARY OF THE INVENTION

By way of experimentation, it has been determined that the simplest method to accomplish microbial intervention at the surface of food products and processing equipment involves the use of steam and chilled water. An economically viable and mechanically robust apparatus adapted for microbial intervention and pasteurization of food product and processing equipment surfaces comprises a chamber in fluid communication with a steam generator which is in turn connected to a controller and timer, a produce temperature sensor, and a power source.

A chilled water source is present in the interior portion of the chamber, and is typically located above a suspension element (e.g., shelf or conveyor belt) which supports the produce or equipment above the bottom surface of the chamber interior. The water source provides water to bathe the produce or equipment at a (temperature from about 2° to about 5° C., if chilled). The source may be located in the interior portion of the chamber, or at the exterior of the chamber, depending on the particular process implemented, and the desires of the user. The water may include a sanitizing agent, including a suitable food and equipment grade sanitizer, such as chlorine, in quantities of about 50 ppm to about 400 ppm.

The steam generator has a steam pipe by which steam is conducted to the chamber. A water inlet valve allows water into the steam generator interior. The water inlet valve is in fluid communication with an orifice and a regulating valve, which ensures that the water volumetric flow never exceeds a preselected level.

The invention also includes a method for microbial intervention and pasteurizing the outer surface of foods and food processing equipment comprising the steps of placing the food or equipment in the chamber, adding steam to the chamber, sensing the temperature of the outer surface of the food or equipment, and adding steam to the chamber until the sensed temperature is about 74° C. Once the temperature reaches 74° C., a 60-second timer is started to ensure that the surface of the produce or equipment is exposed to steam for at least 60 seconds at the required temperature. After this period of time, the outer surface of the produce or equipment may be bathed with chilled water for about 60 seconds. If chilled, the temperature of the water is about 2°–5° C.

The temperature of the food or equipment surfaces may be sensed by placing a thermocouple on the surface of the food or equipment, or by inserting the thermocouple into the food, and sensing the temperature approximately ¼ inch below the food surface. A remote infrared sensor can also be placed or located to detect the surface temperature of the food or equipment, and used to control implementation of the method.

The chamber may be structured as a tunnel with openings at either end for the continuous pasteurization of food on a roller conveyor. In this embodiment, the steam generator is connected to three steam pipes in the steam tunnel and one steam pipe underneath the roller conveyor. These pipes have multiple outlets in order to surround the food with steam from several directions at once. As the food exits the steam tunnel, the food is sprayed with a chilled water bath from a chilled water source outside the tunnel.

The food processing equipment pasteurization system may be structured as a stainless steel bonnet or cover which is lowered over a piece of food processing equipment such as a meat slicer. The equipment sits on a bottom unit which includes a grated floor and drain pans. A steam inlet in the hood allows the steam to enter the bonnet. The steam is controlled by venting handles which allow excess pressure to escape. Steam flow is directed across the surface of the hood via multiple openings. The base unit also contains steam pipes with multiple outlets to allow steam to escape from the hood. Drain pans in the bottom unit collect steam and particles from the equipment.

BRIEF DESCRIPTION OF THE DRAWINGS

A more complete understanding of the structure and operation of the present invention may be had by reference to the following detailed description taken in conjunction with the accompanying drawings, wherein:

FIG. 5 is a schematic diagram of the pasteurization steam tunnel integrated with an industry system set-up;

DETAILED DESCRIPTION OF PRESENTLY PREFERRED EXEMPLARY EMBODIMENTS

Figure 1:
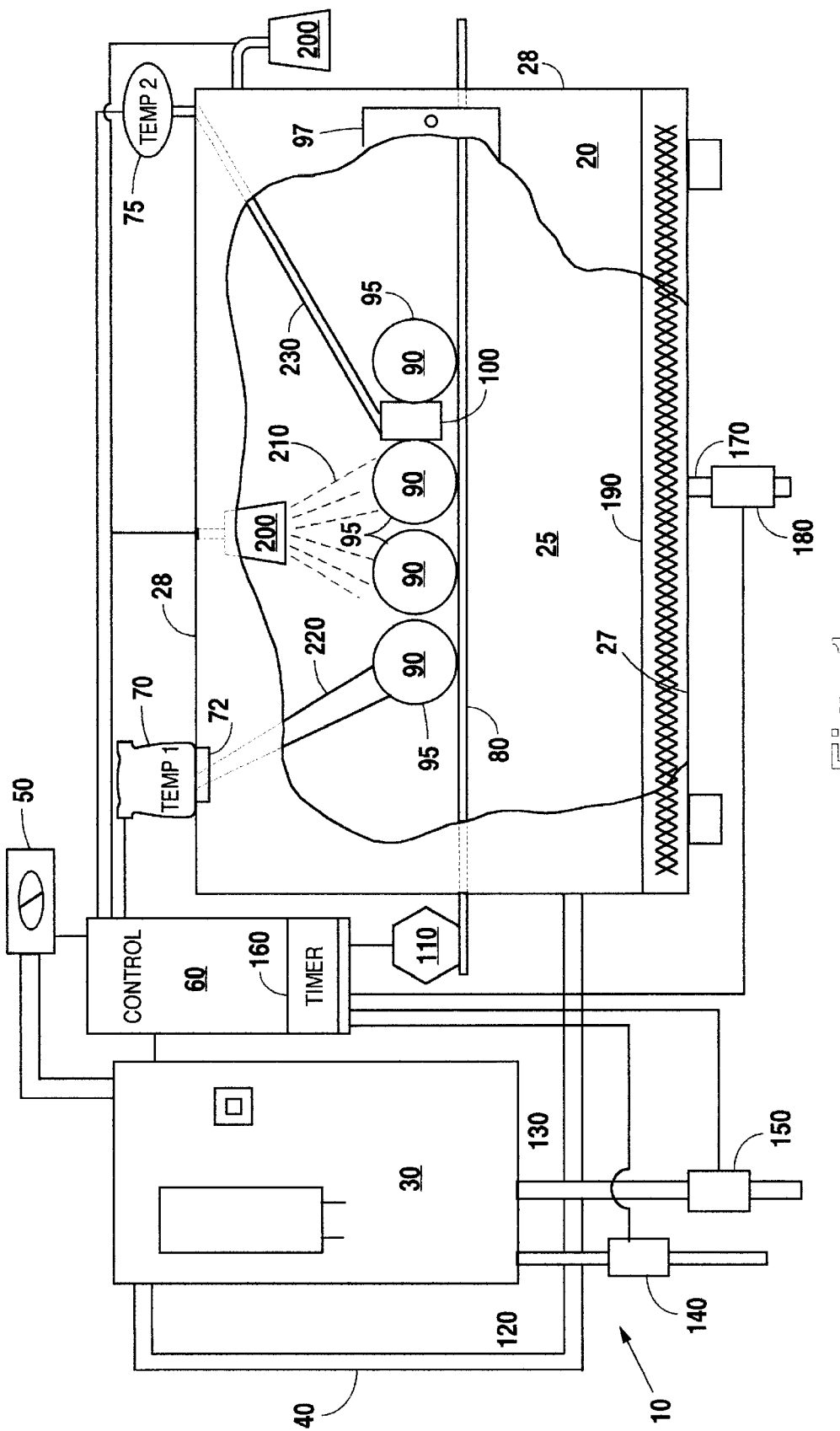
FIG. 1 is a side-cut-away view of the microbial intervention and pasteurization apparatus of the present invention.

The microbial intervention and surface pasteurization apparatus 10 of the present invention can be seen in FIG. 1. The apparatus 10, which is adapted for surface microbial intervention and pasteurization of produce or food processing equipment 90 having an outer surface 95 comprises a chamber 20 with an interior portion 25. A source of chilled water 210, such as a water application nozzle 200. may be located at the interior portion 25, or at the exterior of the chamber 20. The chamber 20 includes a suspension element 80, such as a conveyor or shelf, which is adapted to support the produce or food processing equipment 90 above the bottom surface 27 of the chamber 20. This method of suspending the food or processing equipment 90 prevents contact with fluids 190 that may have come to rest at the bottom surface 27 of the chamber 20. Further, if the suspension element 80 is perforated, chilled water 210 and steam can more easily circulate around the outer surface 95 of the food or processing equipment 90, and drain properly onto the bottom surface 27 of the chamber 20. These fluids 19 may be drained from the bottom surface 27 of the chamber 20 by using the chamber drain 170, which is controlled by a drain valve 180.

A controller 60 is in electrical communication with several components or elements of the apparatus 10. Thus, the controller 60 operates the steam generator 30, several valves 140, 150, and 180; the conveyor drive 110, if necessary; and the chilled water source 200. The controller 60 also senses temperature by way of a remote temperature sensor 70, which may be a remote infra-red sensor, or a proximate temperature sensor 75 which makes use of a thermocouple 100 to measure the temperature of the surface 95 of the food or processing equipment 90. To sense temperature using the remote temperature sensor 70, a port 72, made of glass or other optically transparent material, must be introduced into the wall 28 of the chamber 20.

The steam generator 30 is powered by the power source 50, which is also in electrical communication with the controller 60 and the timer 160. The controller 60 and timer 160 may be separate, or may form an integral unit.

The steam generator 30 has a steam pipe 40 which is fluid communication with the interior portion 25 of the chamber 20. Water is introduced into the steam generator 30 by the water pipe 120, which includes a water inlet valve, which is essentially in fluid communication with the interior portion of the steam generator 30. The steam generator also includes a backflush pipe 130 having a safety valve 150.

Figure 2:
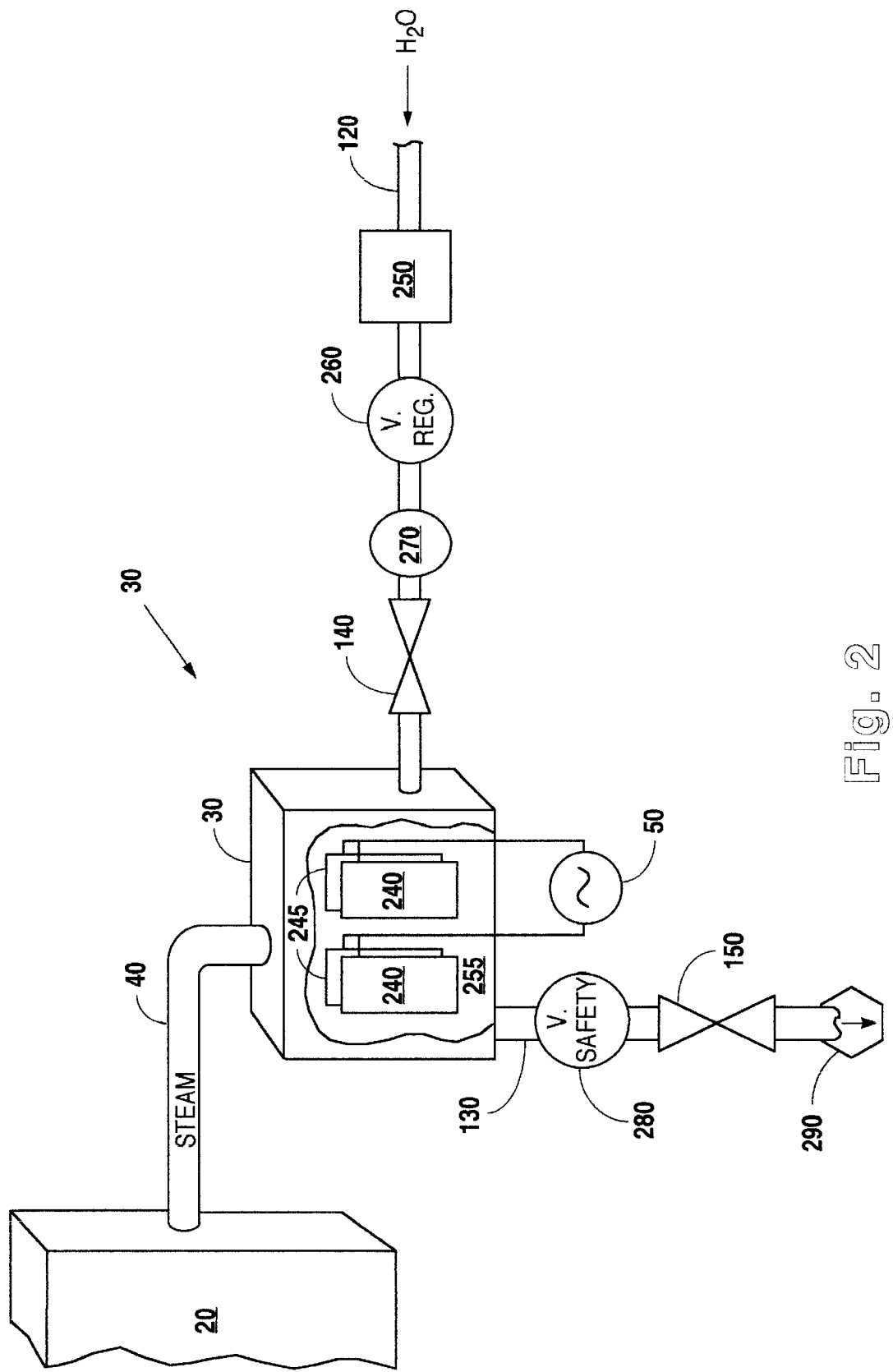
FIG. 2 is a schematic block diagram of the steam generator and its related plumbing.

Turning now to FIG. 2, the steam generator 30 peripheral plumbing elements can be seen. Prior art steam generators used for food products often include inefficient and complex components. The steam generator 30 design of the present invention is simple, reliable, and has the capability to generate steam very quickly. The steam generator 30 makes use of one or more sets or series of plates, such as the first plate pair 240 and the second plate pair 245, connected to a power source 50 to generate steam. The addition of each set of plates increases the quantity of steam generated so that even water having poor conductivity can be used to produce adequate quantities of steam.

During operation, the interior portion 255 of the steam generator 30 is allowed to fill with water. The source of the water is the water pipe 120 that makes use of a filter 250 to provide strained water to the regulating valve 260. An orifice of about 0.033 inches diameter is placed in line with the water inlet pipe 120 to direct the water flow into the interior 255 of the generator 30, and a water inlet valve 140 is used to turn the flow of water on/off.

As the inlet valve 140 is turned on, water is allowed to flow through the water pipe 120, the filter 250, the regulating valve 260, and the orifice 270 into the interior portion 255 of the steam generator 30. The volume of water entering the generator 30, and thus the volume of steam generated, is adjusted by manipulating the regulating valve 260. The non-distilled water which enters the interior portion 255 of the generator 30 provides a complete electrical circuit between the first and second plate pairs 240, 245, allowing a current to flow between them. This current flow serves to heat the plates 240, 245, and generate steam within the generator 30. Since the backflush valve 150 on the backflush pipe 130 is closed at this time, the steam is driven into the steam pipe 40 and enters the chamber 20.

The steam generated is a low pressure steam that eliminates many potential problems associated with boilergenerated steam. As water moves across the heated plates 240, 245, dissolved solids such as calcium, minerals, and salts are deposited in the flowing water. The water flow serves to remove the dissolved solids from the electrodes and prevents accumulation. When there is no more need for steam generation, the inlet valve 140 can be closed and the backflush valve 150 opened so that the water, including deposits, can drain through the backflush pipe with pressure created by an orifice installed in the steam line and backflush valve 150 into the drain 290.

Figure 3:
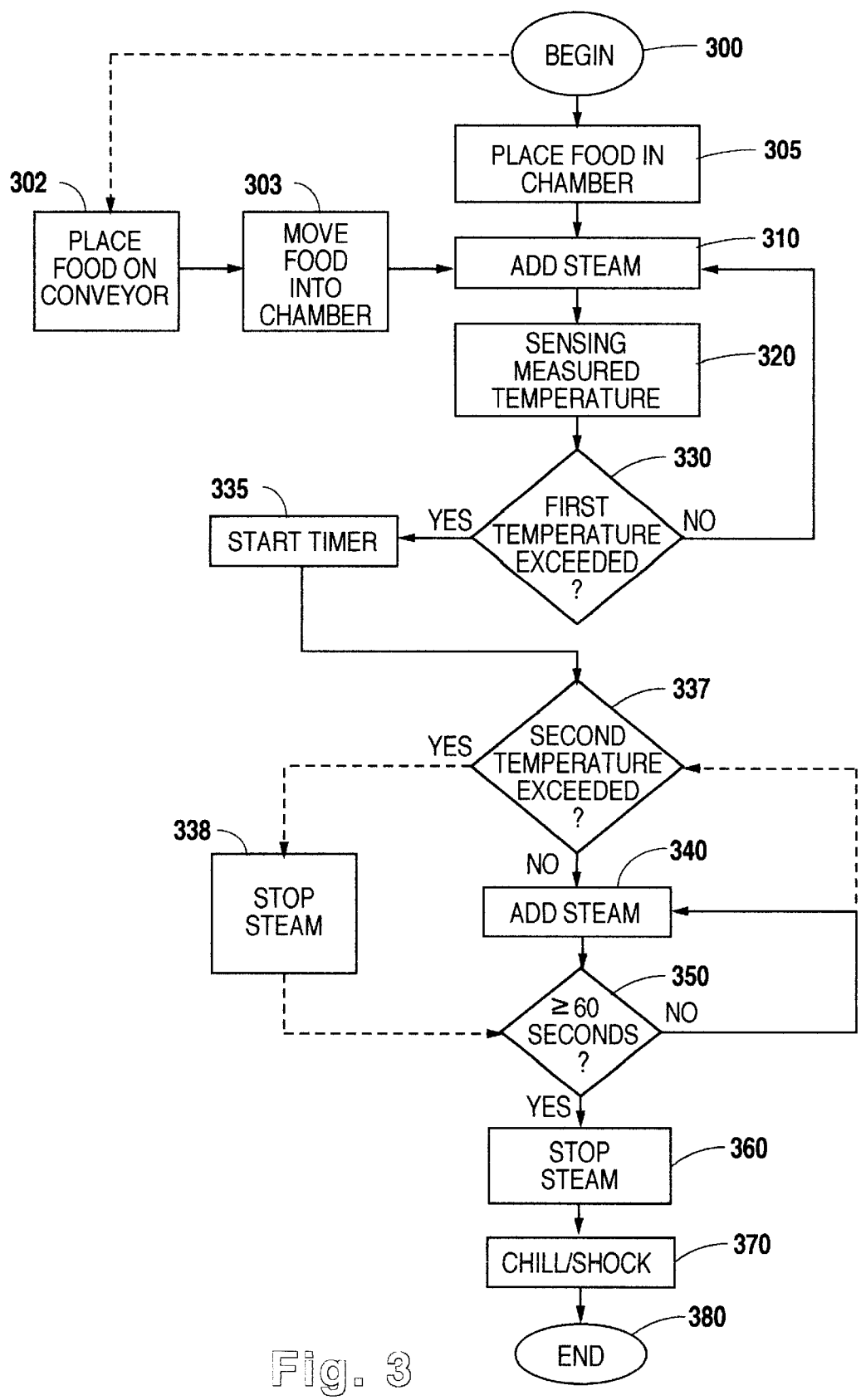
FIG. 3 is a flow chart which illustrates the method of the present invention.

Turning now to FIG. 3, and reviewing FIG. 1, one possible embodiment the method of the present invention can be visualized. The method begins at step 300 by placing food processing equipment or produce in the chamber at step 305 and adding steam to the chamber at step 310. The measured temperature of the food or processing equipment outer surface is sensed at step 320 and a comparison is made as to whether the surface temperature is greater than some first preselected temperature, preferably about 74° C. as shown at step 330. If not, temperature measurements continue to be made and more steam is added until the surface temperature of the food or processing equipment is determined to be greater than or equal to the first preselected temperature, which may be about 74° C.

After reaching the first preselected surface temperature, a timer is started. The timer has a time-out period of about 60 seconds, and steam is added to the chamber on a continuous basis until the end of the 60-second time period. This is illustrated in steps 335, 340 and 350. Steps 337 and 338 are optional, and the method may proceed directly from step 335 to step 340.

After the surface temperature of the food or processing equipment has reached the proper temperature, and is maintained at that preselected temperature for a period of approximately 60 seconds, steam is no longer added to the chamber, as shown in step 360, and the outer surface of the processing equipment or food is bathed with chilled water for about 60 seconds in step 370. This step, which includes bathing the food or processing equipment with water (if chilled, at a temperature of from about 2° C.) to about 5° C., serves to stop the "cooking" effect of the steam (or cools the equipment) and shocks organisms on the surface of the food or equipment to further reduce their numbers. Testing verifies that this method consistently produces a 5-log reduction in the population of microorganisms and bacteria on the surface of food. The method ends at step 380. Alternatively, the water may or may not be chilled, and may include chlorine, or some other suitable food and equipment grade sanitizing agent, in quantities of from about 50 ppm to about 400 ppm.

As shown in FIG. 1, the temperature of the food or equipment 90 can be measured in several different ways. One alternative includes the use of a proximate temperature sensor 75 which is connected to a thermocouple 100 by an electronic temperature signal 230. The thermocouple 100 may be placed on the surface of the food or equipment 90, or located so as to sense the temperature of the food about ¼ inch below the outer surface. Thus, the temperature may be measured on to the outer surface of food or equipment, or at some short distance beneath the outer surface of food.

Another measurement alternative includes the use of a remote temperature sensor 70 operating through a port 72 to obtain an infra-red temperature signal 220 from the surface of the food or equipment 90. The signals from the remote temperature sensor 70, or the proximate temperature sensor 75 are recorded by the controller 60 and used to operate the steam generator 30 and timer 160. Non-contact methods of temperature measurement are preferred, since the possible transfer of organisms between food products using contact methods is obviated. If the suspension element 80 is a conveyor, then food or equipment 90 may be transported into, and out of, the chamber 20 using a conveyor drive 110. Otherwise, a door 97 may be used for direct access to the interior portion 25 of the chamber 20. As noted above, the source of chilled water 200, shown in FIG. 1 as a water application nozzle 200, may be located in the interior portion 25 of the chamber 20, or at the exterior of the chamber 20.

It should be noted that, while some prior art methods describe the application of steam to food products, there is no capability provided to prevent excessive heating of the food. It has been determined through experimentation that the application of steam which produces surface temperatures above about 84° C. significantly affects the organoleptic properties of food products, and derivatives, such as juice. The instant invention, which includes the capability to measure the surface (or sub-surface) temperature of food may include additional steps to enhance the repeatability of microbial intervention and pasteurization results. For example, the method may include the steps of sensing the surface temperature of the food (or equipment, if desired) 90 so that, if temperatures greater than a second preselected temperature, for example, greater than about 84° C. are detected, the steam generator 30 will be shut down so as to prevent further increases in surface temperature. This may occur prior to the end of the 60-second time period for steam application shown in FIG. 3, at steps 337 and 338. Further, different food products may require different preselected temperatures for efficient microbial intervention and pasteurization, and the prevention of adverse effects to organoleptic properties. Thus, the method may include adjusting the surface temperatures from about 74° C. to other, preselected temperatures. The method may also include the steps of placing the food or equipment 90 on a conveyor 80 as step 302, operating the conveyor drive to introduce the food/equipment 90 into the interior portion 25 of the chamber 20 at step 303, and continuing with the method illustrated in FIG. 3, at step 310.

Figure 4A:
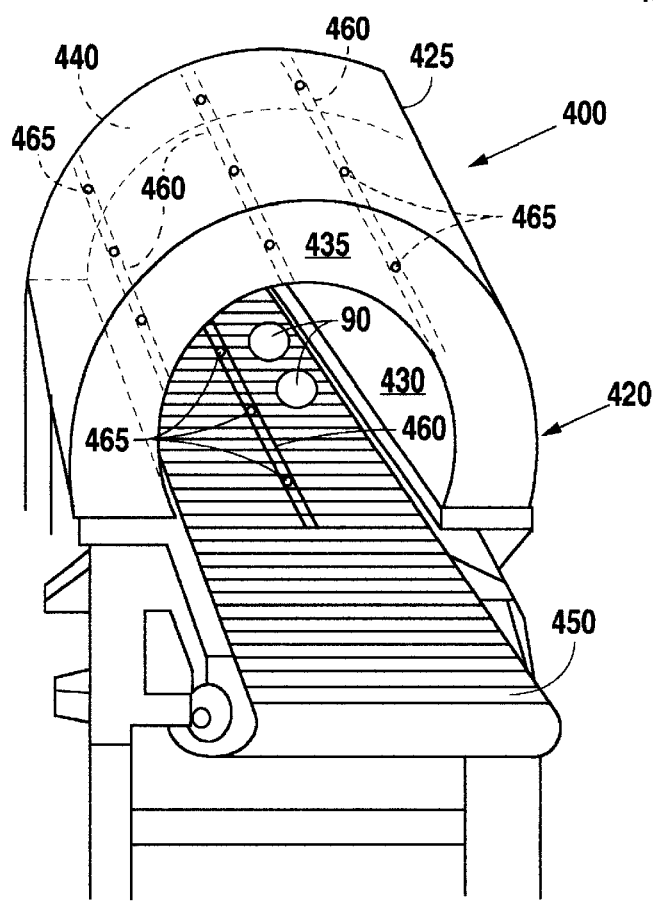
FIGS. 4A, 4B, and 4C illustrate perspective, side cut-away, and top cut-away views, respectively, of the pasteurization steam tunnel and conveyor apparatus.
Figure 4B:
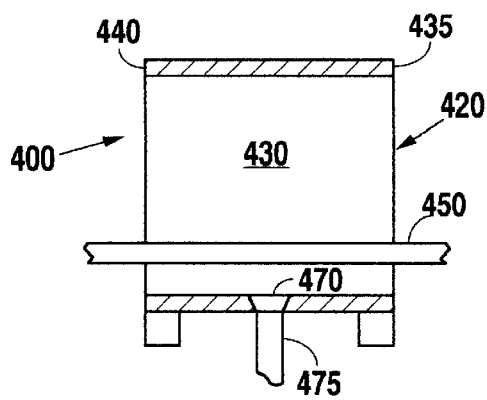
Figure 4C:
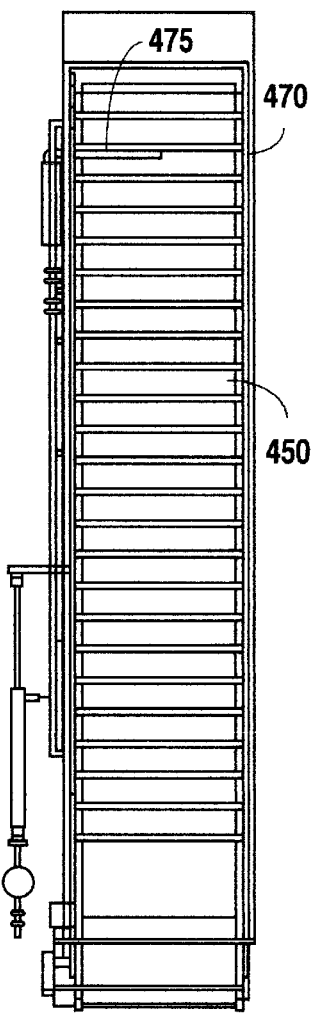

The pasteurization steam tunnel and conveyor apparatus can be seen in FIG. 4. The apparatus 400 comprises a tunnel structure 420 having an outer surface 425, an inner surface 430, an anterior surface 435 and a posterior surface 440. The apparatus also includes a roller conveyor 450 which propels food 90 through the tunnel 420. The tunnel 420 contains multiple pipes 460 which extend the length of the tunnel 420 from anterior surface 435 to posterior surface 440. Each pipe 460 contains multiple openings 465 for the introduction of steam through the inner surface 430 of the tunnel 420 to the food 90 on the conveyor belt 450. An additional pipe 460 runs beneath the roller conveyor 450. The pipe 460 contains multiple openings 465 for the introduction of steam through the openings in the roller conveyor 450. The steam drains onto the bottom surface of the tank drain 470 located underneath the conveyor belt 450 wherein the water collects to drain through the tank drain pipework 475.

Turning now to FIG. 5, the schematic diagram of the pasteurization steam tunnel 400 integrated with an industry system set-up can be seen. This industry design allows the pasteurization steam tunnel 400 to be integrated into an efficient food processing system 500 whereby pasteurized foods are routed via additional conveyor belts into bags or boxes and onto pallets for transfer and delivery. The food 90 is loaded onto a roller conveyor 512 and transported to the in-feed table 515. Next, the food 90 is introduced into the pasteurization steam tunnel 400 (typically by means of another conveyor 510). After the food 90 is rolled out of the steam tunnel 400 and continues to the box loading ramp 520. The boxes 525 are taped at the taping station 530. The food 90 is loaded into the boxes 525, it continues via conveyor 535 to the scale 540 for weighing. The boxes 525 then continue via conveyor 545 to the roller conveyor 547 for transfer to one or more pallets 550. Alternatively, the food 90 is rolled out of the steam tunnel 400 and continues on the conveyor 555 to the accumulation turn table 560 where it is placed in bags 565 by the bagger 570. The bags 565 are transported on the roller conveyor 575 to one or more pallets 580 for transfer and delivery.

Figure 6:
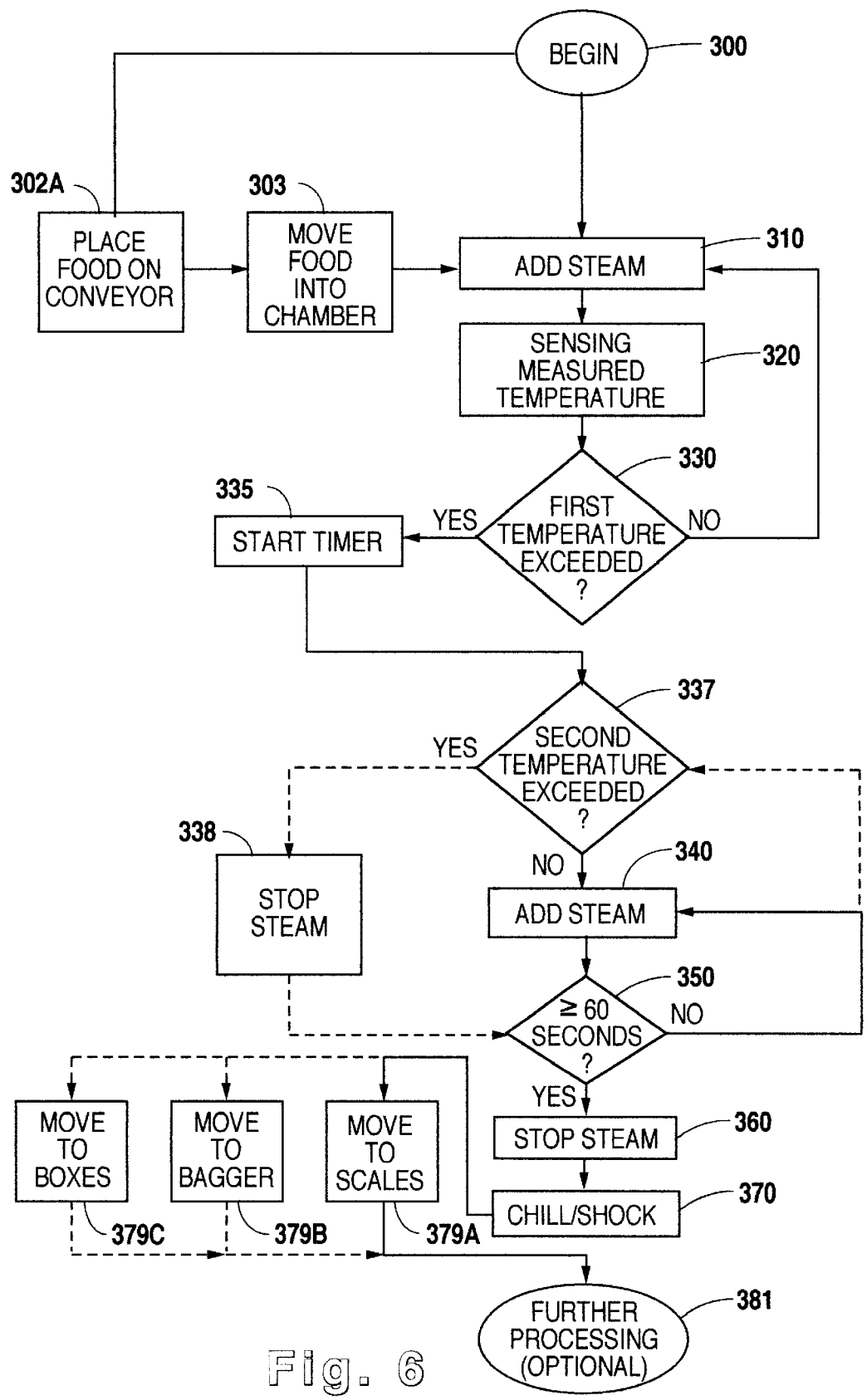
FIG. 6 is a flow chart which illustrates the method of the invention for an industry system set-up utilizing the pasteurization steam tunnel.

Thus, as shown in FIG. 6, the method of the invention may also include the steps of placing the food 90 on conveyor 510 in step 302A, operating the conveyor drive to move the food onto roller conveyor 512 at step 302B, moving the food 90 to the in-feed table 515 at step 302C, introducing the food 90 into the pasteurization steam tunnel 400 at step 303, and continuing with the method steps described in FIG. 3 (steps 310–370). In this embodiment, the method continues after step 370, wherein the food 90 is chilled/shocked, with steps 379A, 379B, or 379C whereby the food 90 proceeds via conveyor to either the boxes 525 in step 379A, the bagger 570 in step 379B, or the scales 540 in step 379C. Further processing may then occur in step 381.

Figure 7A:
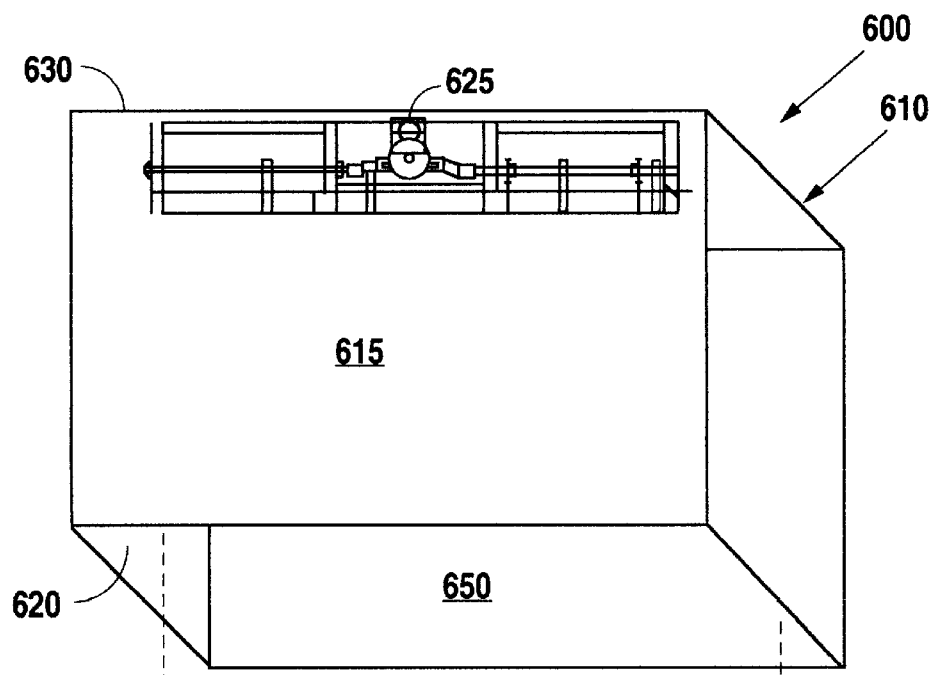
FIGS. 7A and 7B illustrate perspective cut-away and side cut-away views, respectively, of the pasteurization apparatus designed as a steam containment unit.
Figure 7B:
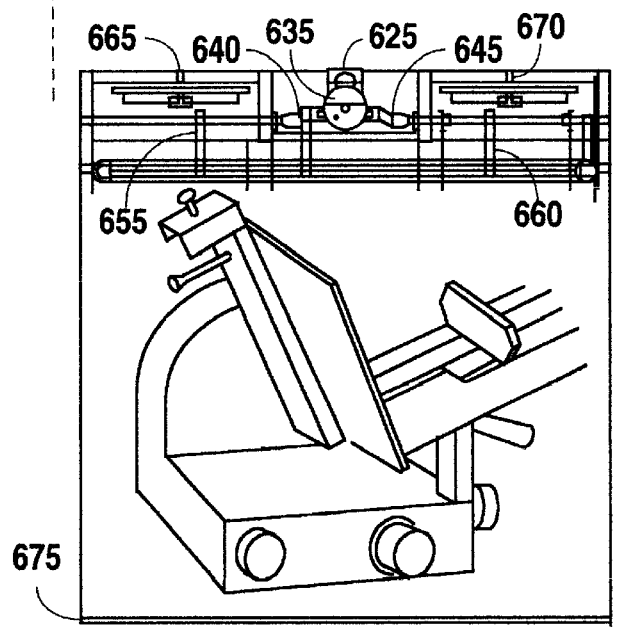

Turning to FIGS. 7A and 7B, the food equipment surface pasteurization system is illustrated as a steam containment unit or chamber 600. The apparatus includes a stainless steel bonnet or cover unit 610 and a bottom or base unit 675. The bonnet 610 has an outer surface 615 and an inner surface 620. The bonnet has one or more steam inlets 625 located in the top wall 630 of the bonnet 610. Steam enters the bonnet 610 through the steam inlets 625 by a pipe 635. The pipe 635 is bifurcated into two smaller pipes 640 and 645 to allow the steam to flow to both sides of the interior 650 of the bonnet 610. Directional steam flow devices 655 and 660 extend from the pipes 640 and 645 to introduce steam into all areas of the bonnet interior 650. Two venting handles 665 and 670 are located in the top wall 630 of the bonnet 610 to facilitate regulation of the steam pressure.

Figure 8:
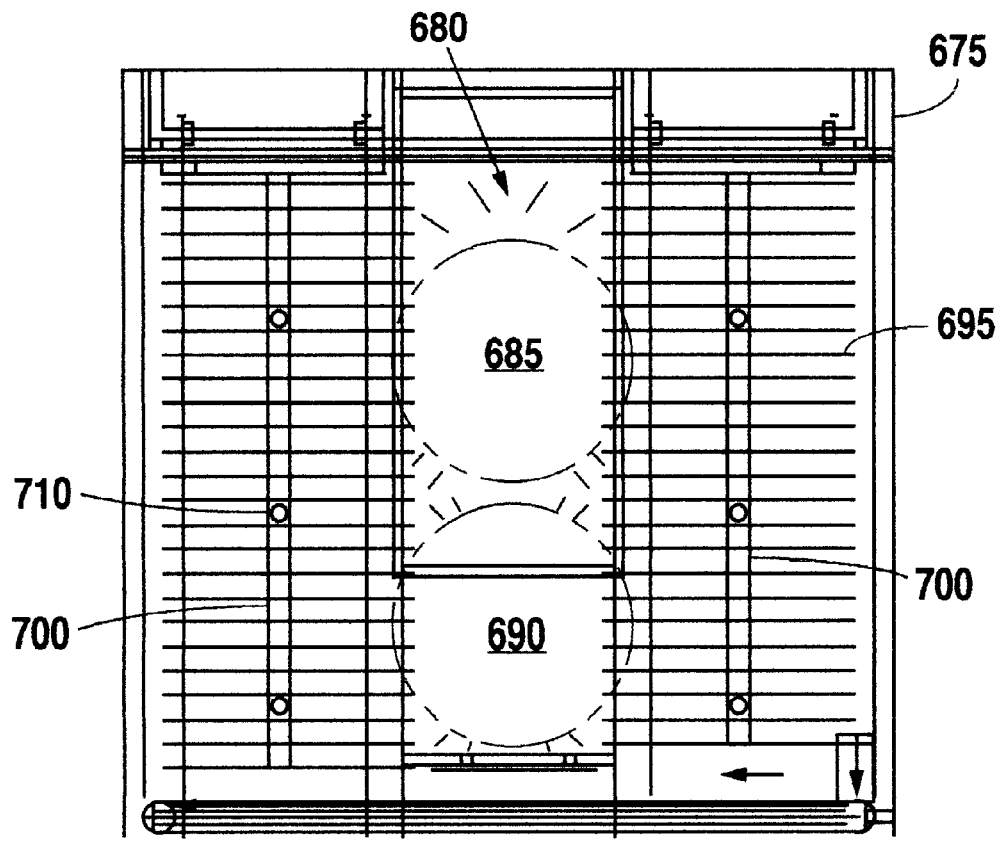
FIG. 8 is an inside view of the bottom of the steam containment unit.

The bottom or base unit 675 can be seen in greater detail in FIG. 8. The bottom floor 680 of the base unit 675 slopes downwardly toward to drain pans 685 and 690. Suspended grates 695 extend across the bottom floor 680 in order to support food or food equipment. Steam outlet pipes 700 are located along the bottom floor 680 under the grates 695. Multiple outlets 710 are placed along the steam outlet pipes 700 in order to allow steam to escape into the interior 650 of the bonnet 610 at various positions.

Many variations and modifications may be made to the disclosed embodiments of the invention without departing from the spirit and principles described herein. All such modifications and variations are intended to be included within the scope of the present invention, as defined by the following claims.

What we claim is:

1. An apparatus for microbial intervention and pasteurization of food processing equipment having an outer surface, comprising:
    a chamber having an interior portion, a bottom surface, and a suspension element for supporting the food processing equipment above the bottom surface;
    a steam generator having a steam pipe, an interior portion, and a water inlet valve, the steam pipe being in fluid communication with the interior portion of the chamber and the interior portion of the steam generator, and the water inlet valve being in fluid communication with the interior portion of the steam generator;
    a chilled water source;
    a controller in electrical communication with the water inlet valve and the chilled water source;
    a timer in electrical communication with the controller;
    a power source in electrical communication with the steam generator, the controller, and the timer; and
    a temperature sensor for sensing the temperature of the outer surface, the sensor being in electrical communication with the controller.

2. The apparatus of claim 1, wherein the chamber includes a drain.

3. The apparatus of claim 1, wherein the chilled water source includes chilled water maintained at a temperature of from about 2° C. to about 5° C.

4. The apparatus of claim 1, wherein the steam generator includes a backflush pipe having a safety valve.

5. The apparatus of claim 1, wherein the suspension element is a shelf.

6. The apparatus of claim 5, wherein the shelf is a porous shelf.

7. The apparatus of claim 1, wherein the suspension element is a conveyor.

8. The apparatus of claim 7, wherein the chamber includes a drain, and the drain is located beneath the conveyor.

9. The apparatus of claim 7, wherein the conveyor is a porous conveyor.

10. The apparatus of claim 1, wherein the controller and the timer form an integral unit.

11. The apparatus of claim 1, wherein the temperature sensor is a thermocouple.

12. The apparatus of claim 1, wherein the temperature sensor is a remote infra-red sensor.

13. The apparatus of claim 1, wherein the chilled water source is located in the interior portion of the chamber.

14. The apparatus of claim 1, wherein the chilled water source is not located in the interior portion of the chamber.

15. The apparatus of claim 1, wherein the steam generator includes a first set of plates and a second set of plates in electronic communication with the power source.

16. The apparatus of claim 1, wherein the water inlet valve is in fluid communication with an orifice.

17. The apparatus of claim 1, wherein the suspension element is a grated floor.

18. The apparatus of claim 1, wherein the chamber includes at least one drain pan.

19. The apparatus of claim 1, wherein the chamber includes a bonnet and a base unit.

20. The apparatus of claim 19, wherein the bonnet has a steam inlet and at least one venting handle for regulation of steam pressure within the bonnet.

21. The apparatus of claim 19, wherein the base unit has a bottom and includes steam outlet pipes located along the bottom.

22. A method for microbial intervention and pasteurizing a food processing equipment having an outer surface comprising the steps of:
    placing the food processing equipment in a chamber;
    adding steam to the chamber;
    sensing a measured temperature of the outer surface;
    adding steam to the chamber if the measured temperature of the outer surface is less than about 74° C., otherwise;
    starting a timer having a timeout period of about 60 seconds;

adding steam to the chamber until the timeout period occurs;

stopping the addition of steam to the chamber.

23. The method of claim 22, including the step of bathing the outer surface with water including a sanitizing agent.

24. The method of claim 22, wherein the step of sensing a measured temperature of the outer surface is accomplished using a thermocouple placed in proximity to the outer surface.

25. The method of claim 22, wherein the step of sensing a measured temperature of the outer surface is accomplished using a remote infra-red sensor.

26. A method for microbial intervention and pasteurizing a food processing equipment having an outer surface comprising the steps of:

placing the food processing equipment in a chamber;

adding steam to the chamber;

sensing a measured temperature of the outer surface;

adding steam to the chamber until the measured temperature of the outer surface is greater than a first preselected temperature;

starting a timer having a timeout period of about 60 seconds; adding steam to the chamber until the timeout period occurs, or the measured temperature of the outer surface becomes greater than a second preselected temperature, whichever occurs first; and bathing the outer surface with water for about 60 seconds after the timer reaches the timeout period.

27. The method of claim 26, wherein the water includes a sanitizing agent.

28. The method of claim 26, wherein the sanitizing agent is a food and equipment grade sanitizer.

29. The method of claim 26, wherein the step of sensing a measured temperature of the outer surface is accomplished using a thermocouple placed in proximity to the outer surface.

30. The method of claim 26, wherein the step of sensing a measured temperature of the outer surface is accomplished using a remote infra-red sensor.

31. The method of claim 26, wherein the first preselected temperature is about 74° C.

32. The method of claim 26, wherein the second preselected temperature is about 84° C.

33. A method for microbial intervention and pasteurizing a food processing equipment having an outer surface comprising the steps of:

adding steam to a steam tunnel;

sensing a measured temperature of the outer surface;

adding steam to the steam tunnel until the measured temperature of the outer surface is greater than a first preselected temperature;

starting a timer having a timeout period of about 60 seconds;

adding steam to the steam tunnel until the timeout period occurs, or the measured temperature of the outer surface becomes greater than a second preselected temperature, whichever occurs first.

34. The method of claim 33, including the step of placing the processing equipment on a roller conveyor within the steam tunnel.

* * * * *